United States Patent
Burkhart (12)

(10) Patent No.: US 6,737,070 B1
(45) Date of Patent: May 18, 2004

(54) METHODS OF INCREASING THE EFFICACY OF PEROXIDES

(76) Inventor: Craig N. Burkhart, 4556 Crossfields Rd., Toledo, OH (US) 43623

( * ) Notice: Subject to any disclaimer, the term of this patent is extended or adjusted under 35 U.S.C. 154(b) by 51 days.

(21) Appl. No.: 10/091,607

(22) Filed: Mar. 6, 2002

Related U.S. Application Data

(60) Provisional application No. 60/273,787, filed on Mar. 6, 2001.

(51) Int. Cl.$^7$ ........................ A61K 7/00; A61K 33/40; A61K 33/26
(52) U.S. Cl. ................ 424/401; 424/400; 424/613; 424/646; 514/859; 514/871; 514/946; 514/947
(58) Field of Search ................ 424/400, 401, 424/613, 646; 514/859, 871, 946, 947

(56) References Cited

U.S. PATENT DOCUMENTS 4,895,727 A * 1/1990 Allen ........................ 424/642

* cited by examiner

*Primary Examiner*—Shelley A. Dodson
(74) *Attorney, Agent, or Firm*—MacMillan, Sobanski & Todd, LLC

(57) ABSTRACT

This invention relates to methods of increasing the efficacy of peroxides such as benzoyl peroxide in the treatment of skin conditions such as acne. In a preferred embodiment, the invention relates to methods of increasing radicals formed by peroxides on/in the skin, more specifically near/in the comedone, for topical use in dermatology. In a specific embodiment, the invention relates to the use of transitional metals such as Cu(1) and ferrous ions-to increase the efficacy of peroxides such as benzoyl peroxide. In another embodiment, the invention relates to a method by which a peroxide such as benzoyl peroxide and its activator are added to the skin surface at the same time. In another embodiment, the invention relates to the use of a more soluble form of peroxide such as benzoyl peroxide to increase its efficacy. In another embodiment, the invention relates to the addition of a side chain to a peroxide such as benzoyl peroxide so that it is activated by light. In a further embodiment, the invention relates to the addition of a tertiary amine to a peroxide such as benzoyl peroxide at the time of skin application, to improve the efficacy of the peroxide. In another embodiment, the invention relates to the addition of dapsone or other material to a peroxide such as benzoyl peroxide to improve its efficacy.

17 Claims, No Drawings

METHODS OF INCREASING THE EFFICACY OF PEROXIDES

CROSS-REFERENCE TO RELATED APPLICATION

This application claims the benefit of U.S. provisional application serial No. 60/273,787, filed Mar. 6, 2001.

BACKGROUND OF THE INVENTION

This invention relates in general to methods of treating skin conditions such as acne, and in particular to methods of increasing the efficacy of peroxides such as benzoyl peroxide in the treatment of skin conditions.

The pathophysiology of acne vulgaris, the most common cutaneous disease, is the consequence of the interplay of follicular hyperkeratinization, bacteria in the follicular canal, and sebum production. The exact mechanism triggering the development of the comedone and the stimuli causing the non-inflamed lesion to become provoked are poorly understood. The microbiology of acne vulgaris and its immunologic ramifications constitute a major thrust of present research in the elucidation of the pathogenesis of inflammatory acne. Within the microbial flora of the pilosebaceous unit, P. acnes is the most meaningful organism in acne causation.

The methods of acne therapy are usually grouped into several categories such as keratolytics, antibacterials, sebosuppressives, and hormones. Benzoyl peroxide (BP) is the most widely used topical agent for acne since its introduction in the 1960's. BP is very effective for the treatment of acne because it is antibacterial, functions as a peeling agent, has comedolytic activity, and reduces free fatty acid levels. Concomitant topical treatment of BP and erythromycin is stated to be superior to BP alone. Such combination therapies are hypothesized to gain their efficacy by the coupled action of two effective treatments.

SUMMARY OF THE INVENTION

This invention relates to methods of increasing the efficacy of peroxides such as benzoyl peroxide in the treatment of skin conditions such as acne. In a preferred embodiment, the invention relates to methods of increasing radicals formed by peroxides on/in the skin, more specifically near/in the comedone, for topical use in dermatology.

In a specific embodiment, the invention relates to the use of transitional metals such as Cu(1) and ferrous ions to increase the formation of peroxide radicals such as benzoyl peroxide radical.

In another embodiment, the invention relates to a method by which a peroxide such as benzoyl peroxide and its activator (or adjunctive agent) are added to the skin surface at the same time (and not days or months before). This ensures that the ingredients are not inactivated or lost strength by being placed together prior to usage.

In another embodiment, the invention relates to the use of a more soluble form of peroxide such as benzoyl peroxide to increase its efficacy.

In another embodiment, the invention relates to the addition of a side chain to a peroxide such as benzoyl peroxide so that it is activated by light.

In a further embodiment, the invention relates to the addition of a tertiary amine to a peroxide such as benzoyl peroxide at the time of skin application, to improve the efficacy of the peroxide. This could include any tertiary amine structure except for an erythromycin structure.

In another embodiment, the invention relates to the addition of dapsone or other material to a peroxide such as benzoyl peroxide to improve its efficacy.

Various advantages of this invention will become apparent to those skilled in the art from the following detailed description of the preferred embodiments.

DETAILED DESCRIPTION OF THE PREFERRED EMBODIMENTS

This invention relates to methods of increasing the efficacy of peroxides such as benzoyl peroxide in the treatment of skin conditions such as acne. In a preferred embodiment, the invention relates to methods of increasing radicals formed by peroxides on/in the skin, more specifically near/in the comedone (but not limited thereto), for topical use in dermatology. The methods use the radicals formed by peroxides such as benzoyl peroxide, optimizing conditions such that the skin/comedone is the only place they are formed as opposed to in a storage container or wherever the benzoyl peroxide happens to be from the time of application to when the benzoyl peroxide breaks down into its radicals or is metabolized).

The methods of the invention may use the principles of photodynamic therapy directed at acne. Instead of forming radicals in cancer cells, the methods form radicals in/by the comedone (skin surface, sebum within P. acnes). Location and timing of formation of radicals is a very important part of the methods.

The methods use the assumption that radicals derived from BP or other peroxides are the most useful in acne therapy (as opposed to reactive oxygen intermediates used in photodynamic therapy).

In a specific embodiment, the invention relates to the use of transitional metals such as Cu(1) and ferrous ions to increase the efficacy of peroxides such as benzoyl peroxide. The use of transitional metals such as Cu(1) and ferrous ions (as alluded to in the text) to increase the efficacy of benzoyl peroxide. It is anticipated that such an addition to benzoyl peroxide would increase the generation of benzoyloxyl radicals.

The transitional metals include all the elements between Group IIA and IIIa in the periodic table. The list includes zinc, cadmiumn, mercury, scandium, titanium, vanadium, chromium, manganese, yttrium, zirconium, niobium, molybdenum, technetium, ruthenium, rhodium, palladium, silver, lanthanum, hafnium, tantalum, tungsten, rhenium, osmium, iridium, platinum, gold, mercury, actinium, unnilquadium, unnilpentium, unnilhexium, and uniseptium.

A few characteristics of transitional metals include:

most are harder and more brittle with higher melting points, boiling points, and heats of vaporization than the non-transitional metals.

their ions and compounds are usually colored.

they form many complex ions.

most exhibit multiple oxidation states.

many of them are paramagnetic, as are many of their compounds.

many of the metals and associated compounds are effective catalysts.

In another embodiment, the invention relates to a method by which a peroxide such as benzoyl peroxide and its activator (or adjunctive agent) are added to the skin surface at the same time (and not days or months before). An example of such would be a better package system in which the various ingredients that would be added to benzoyl peroxide would be put into a dispenser with two or three chamber (depending upon the number of items combined) to separate the product's ingredients so they do not interact until the instant you apply them to one's acne. This separation would ensure that the ingredients are not inactivated or lost strength by being placed together prior to usage.

Another example of such a system would be benzoyl peroxide (bp) dissolved in a hydrophobic solvent and the activator in a polar solvent. The BP and activator wouldn't meet until applied onto the skin surface. Lipophilic carriers are well known in the art. For an example of the activator in a hydrophilic solvent, both protic and aprotic solvents are included. Protic solvents such as methanol, ethanol, forinamide, N-methylformamide, and water, a hydrogen is attached to the electronegative part of the reagent. The hydrogen has a proton-like character and strongly reacts with anionic nucleophiles. Aprotic solvents do not contain positively polarized hydrogens. These include acetone, acetonnitrile, N,N-dimethylformarnide, DMSO, hexamaethylphophoric triamide—the aprotic solvents increase the reactivity of nucleophiles in SN2 reactions (the possible mechanism of radical formation by the BP tertiary amine combination).

Retin A micro is an example of a product released by a polymer. The retin A is stored in a small polymer bead. After application of these beads onto the skin, retin A slowly diffuses out of the polymer and into the skin. The invention would have the activator of benzoyl peroxide radical formation contained in a similar polymer. The activator would be slowly released (by diffusion or breakdown of the polymer) into the skin allowing it to react with BP. Alternatively, the BP could be stored in and released from the polymer. Or, both the activator and BP could be released from their own individual polymers to react when the meet (in the environment of the skin/comedone).

In another embodiment, the invention relates to the use of a more soluble form of peroxide such as benzoyl peroxide to increase its efficacy. The use of a more soluble form of benzoyl peroxide. The present-day products actually use benzoyl peroxide in the form of crystals. We are able to solubilize benzoyl peroxide either by altering its hydric solvents, or by adding a side chain to its structure.

In another embodiment, the invention relates to the addition of a side chain to a peroxide such as benzoyl peroxide so that it is activated by light. We could also add a side chain to benzoyl peroxide so that it is activated by light.

In a further embodiment, the invention relates to the addition of a tertiary amine to a peroxide such as benzoyl peroxide at the time of skin application, to improve the efficacy of the peroxide. This could include any tertiary amine structure except for an erythromycin structure. We believe that benzoyl peroxide efficacy can be improved by adding a tertiary amine at the time of skin application. Therefore, we would be including all substances (and chemicals) which have a tertiary amine within the provisional patent, be they antibiotics or whatever. The invention would include all tertiary amine structures, save for the erythromycin structure that is presently used in a commercial product named benzymycin.

Some nonlimiting examples of tertiary amines include Alfuzosin, Alimemazine, Analgesic drug (Reference 97), Atropine, alpha,alpha-bis [3-(N-benzyl-N-methyl-carbamoyl)-piperidino]-p-xylene dihydrobromide, Bupivacaine, cis-trans-Cavinton, Cloperastine, Cyamemeazine, Cyclopentolate, 2-(4,5-dihydro-1H-imidazol-2-yl)-2-propyl-1,2,3,4-tetrahydropyrrolo]3,2,1-hi [-indole, 1-decyl-3-(N,N-diethylcarbamoyl)piperidine hydrobromide, Diltiazem, Dimethindene, Diperodone, Disopyramide, Disopyamide, semipreparative, Dixyrazine, Doxazosin, Dropropizine, Hydroxychloroquine and metabolites, Ketoconazole, Laudanosine, Marcaine, Medetomidine, Mepivacaine, Mepivacaine (micro column), Meptazinol, Methadon, Nefopam, Nicotine, Omeprazole, Oxybutynin, Oxyphencyclimide, Pheniramine, 3-PPP, Procyclidine, Promethazine, Proxyphylline, Remoxipride, Tetrahydrozoline, Tetramisole, Tetramisole (micro column), Thioridazine ring-sulphoxide, Tolperisone, Trihexyphenidyl, Trimipramine, Tropicamide, Vamicamide, Verapamil, and Vinca alcaloids. The structures and other characteristics of these tertiary amines can be found on the internet at www.chromtech.se/tertiary.htm. The listed amines are all drugs, but the methods of the invention are not limited to just drugs—any tertiary amine would work.

Along with transition metals, tertiary amines potentiate radical formation by BP. A possible mechanism involves reaction of the amine and BP by a $S_N2$ mechanism. The intermediate thus formed thermally decomposes to benzoyloxy radicals and an amine radical cation. The benzoyloxy radicals may further decompose into phenyl radicals. All of these radicals can react with biological molecules possibly causing some biological effect.

In another embodiment, the invention relates to the addition of dapsone to a peroxide such as benzoyl peroxide to improve its efficacy. Heme is a protoporphyrin. P. acnes actually produces protoporphyrins. 5-aminolevulinlc acid (ALA) increases protoporphyrin production by P. acnes. ALA is the same stuff used in photodynamic chemotherapy and photodynamic antimicrobial chemotherapy. Methylene blue, toluidine blue O, phthalocyanine, and haematoporphyrin derivative could also be used. Phenothiazinium dyes could also be used. These materials might work by depleting the antioxidant levels in/around the comedone allowing the BP derived radicals to reach the comedone or spread further throughout the comedone.

Viagra (sildenafil) increases NO production by blood vessels (and maybe the skin). It is an example of a molecule inducing the skin to produce a benzoyl peroxide activator.

Testing and Discussion

Objective: The purpose was to compare radical activity of BP alone and with various antibiotics to determine whether BP and antibiotics may be chemically synergistic.

Methods: Polymerization of tetra ethylene glycol dimethacrylate was used as a test of BP radical activity. Solutions of BP, antibiotics, and BP and antibiotics were made at 3% w/w in tetraethylene glycol dimethacrylate. All of the antibiotics except erythromycin (ERY) were obtained from prescription pills, which were crushed in a crucible. The portion of the pills that disolved in tetraethylene glycol dimethacrylate were used in the experiment. ERY was obtained in powdered form from Benzamycin® acne treatments. Aliquots of ten drops of these solutions were placed in an eight well plastic plate. The samples were heated in an oven that maintained a temperature range between 90 to 100 degrees Celsius. After various amounts of time the samples were taken out of the oven and tested for gel formation. Polymerization of tetraethylene glycol dimethacrylate was detected visually by swirling a spatula in the solutions. Gelling constituted an indicator of BP radical activity.

Results: The results suggest that radical activity increases upon addition of certain antibiotics, such as erythromycin, to a solution of BP. ERY, minocycline (Vectrin®), and levofloxacin (Levaquin®) in combination with BP caused the tetraethylene glycol dimethacrylate to polymerize the fastest. This is assumed to be due to elevated BP radical formation. Agents that did not augmnent BP radical activity included doxycycline (Monodox®), and trovofloxacin (Trovan®). Upon storage in a dark room at room temperature, the ERY-BP combination gelled within an hour. The Vectring®-BP, Diflucang®-BP, Trovan®-BP, Monodox®-BP, and Levaquin®-BP combinations did not gel within six hours. Zithromycin® (a prescription drug containing a macrolide similar to ERY) in combination with BP also gelled within an hour when stored in a dark room at room temperature. Furthermore, Zithromycin®-BP and ERY®-BP solutions gelled within an hour when stored in a refrigerator. Zithromycin® has not been tested yet at higher temperatures.

Discussion: BP induces a variety of biological effects. BP can inhibit metabolic cooperation, alter protein synthesis, induce omithine decarboxylase activity, cause DNA strand breaks, suppress DNA synthesis, and may interfere with mitochondrial respiration. Several of these effects, such as DNA strand breaks, may be caused by BP-derived radicals. Thus, acne treatments that increase the radical activity of BP may be more effective.

Tertiary amines potentiate radical formation by BP. A possible mechanism involves reaction of the amine and BP by a $S_N2$ mechanism. The intermediate thus formed thermally decomposes to benzoyloxy radicals and an amine radical cation. The benzoyloxy radicals may further decompose into phenyl radicals. All of these radicals can react with biological molecules possibly causing some biological effect. Of the antibiotics tested, ERY, doxycycline (Monodox®), minocycline (Vectrin®), levofloxacin (Levaquin®), and trovofloxacin (Trovan®) contain tertiary amines. ERY-BP, Levaquin®-BP, and Vectrin®-BP combinations all behaved as would be expected as they demonstrated faster kinetics for radical formation than BP alone.

Contaminants and solubility may have caused the unexpected results from the Monodox®-BP and Trovan®-BP combinations. The extra chemicals contained in the pills may have dissolved in the tetraethylene glycol dimethacrylate and acted as plastisizers or radical scavengers, thus, hiding any enhanced radical formation by the antibiotic-BP combination. On the other hand, the contaminants may have accelerated the formation of BP-derived radicals. The contaminants may have affected the results for the Levaquin®-BP and Vectrin®-BP combinations as well. Furthermore, some of the antibiotics may not have dissolved in the tetraethylene glycol dimethacrylate, thus, preventing them from being involved in the experiment as only dissolved material was transferred to the plastic plate for testing.

The most impressive result was the speed that the ERY-BP and Zithromycin®-BP solutions gelled at room temperature and below. The speed of reaction between the macrolides and BP insinuates that all the BP in Benzamycin® may be completely depleted by the time a patient picks up his/her prescription to the time it is applied to his/her body. As Benzamycin® is a very effective drug for the treatment of acne, a novel drug may be formed as a product of reactions of BP and ERY with each other and/or other components in Benzamycin® that is very effective against acne. Finding this chemical may result in the discovery of improved acne treatments that do not require BP. As Zithromycin® similarly increased BP radical formation, it is probable that many macrolides mixed with BP are effective drugs for the treatment of acne.

It may be true that the BP is protected from ERY while stored in its container. For example, much of BP is in a less reactive crystalline form while in acne creams, where as it was fully dissolved in these experiments. Upon application to the skin these crystals of BP may dissolve and react with ERY producing radicals. Depending on where these radicals are formed DNA strand breaks, lipid peroxidation, or other effects may occur.

Conclusion: Radical activity of BP in tetraetylene glycol dimethacrylate is of increased when tested in consort with several antibiotics, such as the macrolides. We propose that the tertiary amines contained on certain antibiotics are responsible for catalysis of BP radical formation. If increased radical formation correlates with enhanced biological effect, then these data reveal the possibility of biological synergism in mixtures of BP and antibiotics. An understanding of the mechanism of catalysis of BP radical formation by antibiotics may lead to the discovery of improved treatments for acne.

In accordance with the provisions of the patent statutes, the principle and mode of operation of this invention have been explained and illustrated in its preferred embodiment. However, it must be understood that this invention may be practiced otherwise than as specifically explained and illustrated without departing from its spirit or scope.

What is claimed is:

1. A method of topically treating a skin condition comprising applying to the skin a combination of a peroxide and a tertiary amine, with the exclusion of erythromycin, the tertiary amine increasing radicals formed by the peroxide on/in the skin to thereby increase the efficacy of the peroxide in the treatment of the skin condition.

2. A method according to claim 1 wherein the peroxide is benzoyl peroxide.

3. A method according to claim 2 wherein the skin condition is acne.

4. A method according to claim 2 wherein the benzoyl peroxide and the tertiary amine react by an $S_N2$ mechanism to produce an intermediate that decomposes to benzoyloxy radicals and an amine radical cation.

5. A method according to claim 1 wherein the tertiary amine is an antibiotic.

6. A method according to claim 3 wherein the tertiary amine is an antibiotic.

7. A method according to claim 1 wherein the radicals are increased in the comedone of the skin.

8. A method of topically treating a skin condition comprising applying to the skin a combination of a peroxide and a tertiary amine, with the exclusion of erythromycin, the tertiary amine increasing radicals formed by the peroxide on/in the skin to thereby increase the efficacy of the peroxide in the treatment of the skin condition, wherein the peroxide and the tertiary amine are combined in a manner such that the radicals are formed on/in the skin and not prior to application of the peroxide and the tertiary amine to the skin.

9. A method according to claim 8 wherein the peroxide and the tertiary amine are combined at the time of their application to the skin.

10. A method according to claim 8 wherein the peroxide is dissolved in a hydrophobic solvent and the tertiary amine is dissolved in a polar solvent.

11. A method according to claim 8 wherein at least one of the peroxide and the tertiary amine is contained in a slow release polymer.

12. A method according to claim 8 wherein the peroxide is benzoyl peroxide.

13. A method according to claim 12 wherein the skin condition is acne.

14. A method according to claim 12 wherein the benzoyl peroxide and the tertiary amine react by an $S_N2$ mechanism to produce an intermediate that decomposes to benzoyloxy radicals and an amine radical cation.

15. A method according to claim 8 wherein the tertiary amine is an antibiotic.

16. A method according to claim 8 wherein the radicals are increased in the comedone of the skins.

17. A method of topically treating acne comprising applying to the skin a combination of benzoyl peroxide and an antibiotic having a tertiary amine, with the exclusion of erythromycin, the tertiary amine increasing radicals formed by the benzoyl peroxide on/in the skin to thereby increase the efficacy of the benzoyl peroxide in the treatment of the acne, wherein the benzoyl peroxide and the antibiotic are combined in a manner such that the radicals are formed on/in the skin and not prior to application of the benzoyl peroxide and the antibiotic to the skin.

* * * * *